United States Patent
Hopkins et al.

(10) Patent No.: US 7,594,901 B2
(45) Date of Patent: Sep. 29, 2009

(54) SURGICAL CASSETTE WITH MULTI AREA FLUID CHAMBER

(75) Inventors: Mark A. Hopkins, Mission Viejo, CA (US); Shawn X. Gao, Irvine, CA (US)

(73) Assignee: Alcon, Inc., Hunenberg (CH)

( * ) Notice: Subject to any disclaimer, the term of this patent is extended or adjusted under 35 U.S.C. 154(b) by 175 days.

(21) Appl. No.: 11/491,630

(22) Filed: Jul. 24, 2006

(65) Prior Publication Data

US 2007/0049898 A1 Mar. 1, 2007

Related U.S. Application Data

(63) Continuation-in-part of application No. 11/158,238, filed on Jun. 21, 2005, now Pat. No. 7,524,299, and a continuation-in-part of application No. 11/384,702, filed on Mar. 20, 2006.

(51) Int. Cl.
*A61M 3/00* (2006.01)
*A61M 37/00* (2006.01)
*A61B 19/00* (2006.01)

(52) U.S. Cl. .................. 604/65; 604/131; 604/403

(58) Field of Classification Search ............... 604/27, 604/30, 403, 65–67; 417/477.2
See application file for complete search history.

(56) References Cited

U.S. PATENT DOCUMENTS

| | | | |
|---|---|---|---|
| 3,742,934 A | 7/1973 | Holbrook et al. | |
| 4,041,947 A | 8/1977 | Weiss et al. | |
| 4,210,029 A | 7/1980 | Porter | |
| 4,444,548 A | 4/1984 | Andersen et al. | |
| 4,548,205 A | 10/1985 | Armeniades et al. | |
| 4,626,248 A * | 12/1986 | Scheller | 604/319 |
| 4,722,350 A | 2/1988 | Armeniades et al. | |
| 4,758,238 A | 7/1988 | Sundblom et al. | |
| 4,823,552 A | 4/1989 | Ezell et al. | |
| 4,841,984 A | 6/1989 | Armeniades et al. | |
| 5,041,096 A | 8/1991 | Beuchat et al. | |
| 5,098,387 A | 3/1992 | Wiest et al. | |
| 5,106,366 A | 4/1992 | Steppe | |
| 5,141,493 A | 8/1992 | Jacobsen et al. | |
| 5,242,404 A | 9/1993 | Conley et al. | |
| 5,267,956 A | 12/1993 | Beuchat | |
| 5,286,262 A | 2/1994 | Herweck et al. | |
| 5,322,504 A | 6/1994 | Doherty et al. | |
| 5,364,342 A | 11/1994 | Beuchat et al. | |
| 5,380,280 A | 1/1995 | Peterson | |
| 5,399,166 A | 3/1995 | Laing | |
| 5,520,652 A | 5/1996 | Peterson | |
| 5,582,601 A | 12/1996 | Wortrich et al. | |
| 5,584,824 A | 12/1996 | Gillette et al. | |
| 5,674,194 A | 10/1997 | Jung et al. | |
| 5,676,650 A | 10/1997 | Grieshaber et al. | |
| 5,747,824 A | 5/1998 | Jung et al. | |
| 5,865,764 A | 2/1999 | Moorhead | |
| 5,899,674 A | 5/1999 | Jung et al. | |
| 6,059,544 A | 5/2000 | Jung et al. | |

(Continued)

*Primary Examiner*—Nicholas D Lucchesi
*Assistant Examiner*—Rebecca E Eisenberg
(74) *Attorney, Agent, or Firm*—W. David Lee

(57) ABSTRACT

A surgical cassette having an aspiration chamber or infusion chamber with a sensing portion and a storage portion. The sensing portion has a small transverse cross sectional area and facilitates accurate fluid level measurements. The storage portion has a larger transverse cross sectional area to facilitate fluid storage.

4 Claims, 2 Drawing Sheets

U.S. PATENT DOCUMENTS

| | | |
|---|---|---|
| 6,261,283 B1 | 7/2001 | Morgan et al. |
| 6,293,926 B1 | 9/2001 | Sorensen et al. |
| 6,561,999 B1 | 5/2003 | Nazarifar et al. |
| 6,572,349 B2 | 6/2003 | Sorensen et al. |
| 6,740,074 B2 | 5/2004 | Morgan et al. |
| 6,962,488 B2 | 11/2005 | Davis et al. |
| 6,986,753 B2 | 1/2006 | Bui |
| 2002/0019607 A1 | 2/2002 | Bui |
| 2003/0204166 A1* | 10/2003 | Sorensen et al. ......... 604/93.01 |
| 2004/0256409 A1* | 12/2004 | Proulx ........................ 222/64 |

* cited by examiner

SURGICAL CASSETTE WITH MULTI AREA FLUID CHAMBER

This application is a continuation-in-part of U.S. application Ser. No. 11/158,238, filed Jun. 21, 2005, now U.S. Pat. No. 7,524,299 entitled "Aspiration Control", and a continuation-in-part of U.S. application Ser. No. 11/384,702, filed Mar. 20, 2006, entitled "Surgical Cassette with Bubble Separating Structure".

FIELD OF THE INVENTION

The present invention generally pertains to a surgical cassette for use with microsurgical systems, and more particularly to such cassettes for use with ophthalmic microsurgical systems.

DESCRIPTION OF THE RELATED ART

During small incision surgery, and particularly during ophthalmic surgery, small probes are inserted into the operative site to cut, remove, or otherwise manipulate tissue. During these surgical procedures, fluid is typically infused into the eye, and the infusion fluid and tissue are aspirated from the surgical site. The types of aspiration systems used, prior to the present invention, were generally characterized as either flow controlled or vacuum controlled, depending upon the type of pump used in the system. Each type of system has certain advantages.

Vacuum controlled aspiration systems are operated by setting a desired vacuum level, which the system seeks to maintain. Flow rate is dependent on intraocular pressure, vacuum level, and resistance to flow in the fluid path. Actual flow rate information is unavailable. Vacuum controlled aspiration systems typically use a venturi or diaphragm pump. Vacuum controlled aspiration systems offer the advantages of quick response times, control of decreasing vacuum levels, and good fluidic performance while aspirating air, such as during an air/fluid exchange procedure. Disadvantages of such systems are the lack of flow information resulting in transient high flows during phacoemulsification or fragmentation coupled with a lack of occlusion detection. Vacuum controlled systems are difficult to operate in a flow controlled mode because of the problems of non-invasively measuring flow in real time.

Flow controlled aspiration systems are operated by setting a desired aspiration flow rate for the system to maintain. Flow controlled aspiration systems typically use a peristaltic, scroll, or vane pump. Flow controlled aspiration systems offer the advantages of stable flow rates and automatically increasing vacuum levels under occlusion. Disadvantages of such systems are relatively slow response times, undesired occlusion break responses when large compliant components are used, and vacuum can not be linearly decreased during tip occlusion. Flow controlled systems are difficult to operate in a vacuum controlled mode because time delays in measuring vacuum can cause instability in the control loop, reducing dynamic performance.

One currently available ophthalmic surgical system, the MILLENIUM system from Storz Instrument Company, contains both a vacuum controlled aspiration system (using a venturi pump) and a separate flow controlled aspiration system (using a scroll pump). The two pumps can not be used simultaneously, and each pump requires separate aspiration tubing and cassette.

Another currently available ophthalmic surgical system, the ACCURUS® system from Alcon Laboratories, Inc., contains both a venturi pump and a peristaltic pump that operate in series. The venturi pump aspirates material from the surgical site to a small collection chamber. The peristaltic pump pumps the aspirate from the small collection chamber to a larger collection bag. The peristaltic pump does not provide aspiration vacuum to the surgical site. Thus, the system operates as a vacuum controlled system.

Despite these conventional systems, a need continues to exist for improved aspiration and infusion fluidics in an ophthalmic surgical system.

SUMMARY OF THE INVENTION

The present invention relates to a surgical cassette having an aspiration or infusion chamber disposed therein. The chamber includes a lower sensing portion for enabling accurate measurements of fluid level change, and an upper storage portion to enable storage of fluids during surgical procedures. The transverse cross sectional area of the sensing portion is smaller than the transverse cross sectional area of the storage portion.

BRIEF DESCRIPTION OF THE DRAWINGS

For a more complete understanding of the present invention, and for further objects and advantages thereof, reference is made to the following description taken in conjunction with the accompanying drawings, in which.

DETAILED DESCRIPTION OF THE PREFERRED EMBODIMENTS

Figure 1:
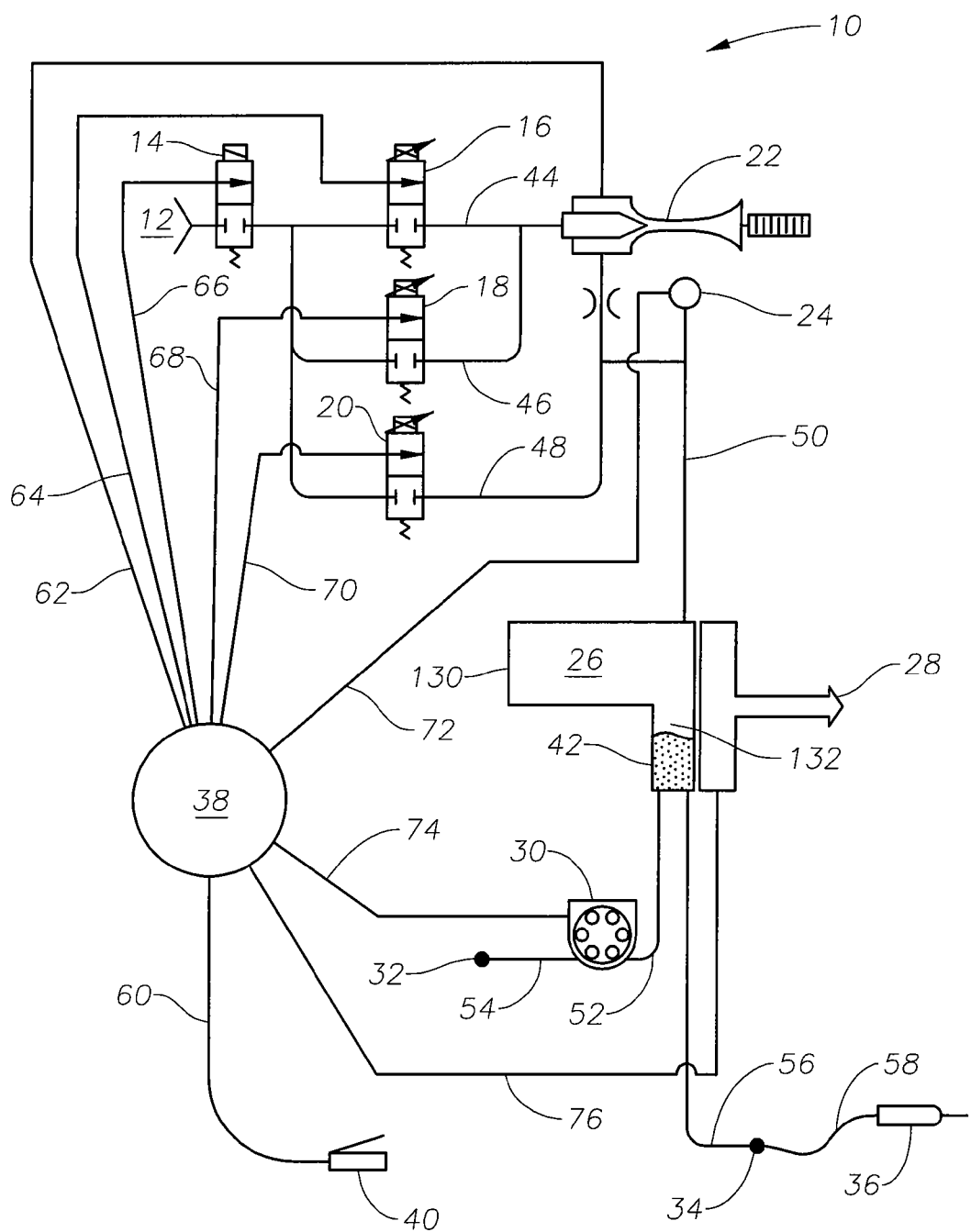
FIG. 1 is a schematic diagram illustrating aspiration control in a microsurgical system.
Figure 3:
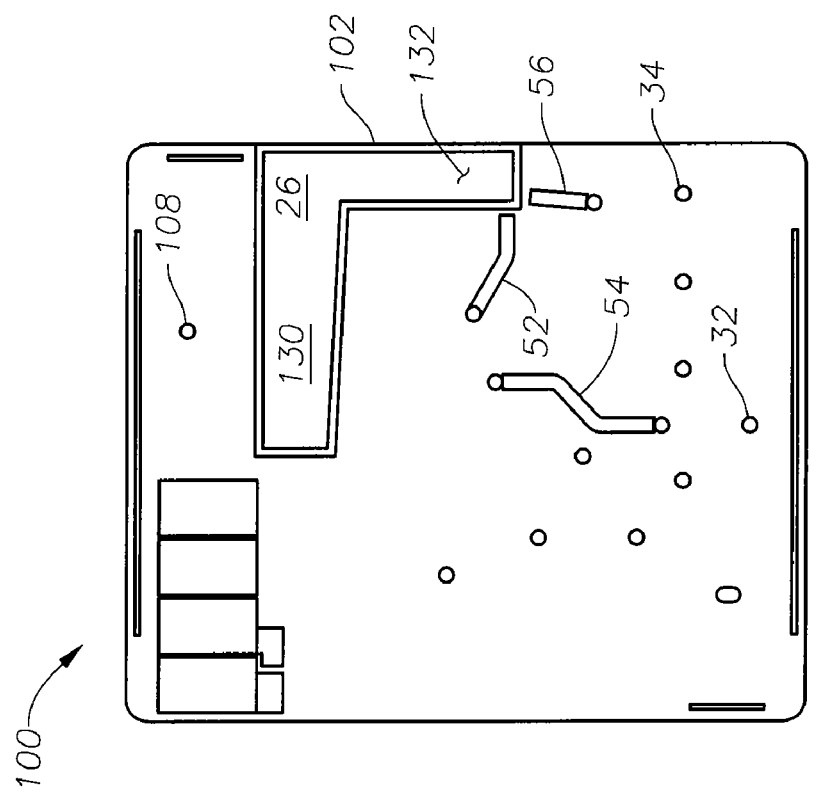
FIG. 3 is a rear view of the surgical cassette body of FIG. 2.
Figure 2:
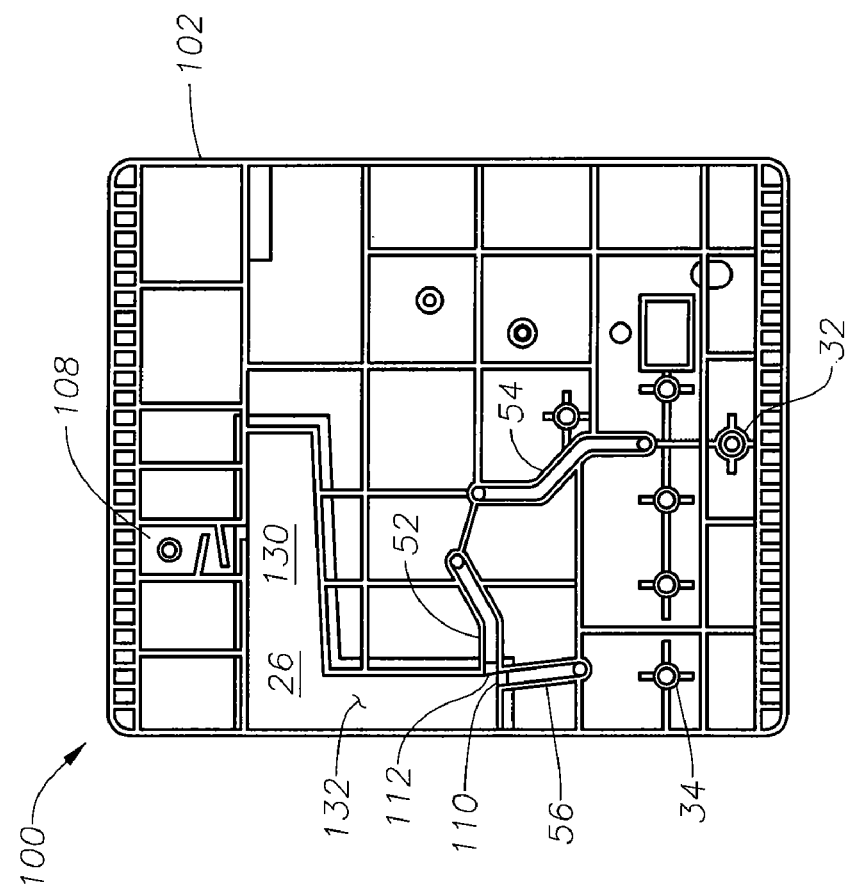
FIG. 2 is a front view of a surgical cassette body.

The preferred embodiments of the present invention and their advantages are best understood by referring to FIGS. 1-3 of the drawings, like numerals being used for like and corresponding parts of the various drawings.

Microsurgical system 10 includes a pressurized gas source 12, an isolation valve 14, a vacuum proportional valve 16, an optional second vacuum proportional valve 18, a pressure proportional valve 20, a vacuum generator 22, a pressure transducer 24, an aspiration chamber 26, a fluid level sensor 28, a pump 30, a collection bag port 32, an aspiration port 34, a surgical device 36, a computer or microprocessor 38, and a proportional control device 40. The various components of system 10 are fluidly coupled via fluid lines 44, 46, 48, 50, 52, 54, 56, and 58. The various components of system 10 are electrically coupled via interfaces 60, 62, 64, 66, 68, 70, 72, 74, and 76. Valve 14 is preferably an "on/off" solenoid valve. Valves 16-20 are preferably proportional solenoid valves. Vacuum generator 22 may be any suitable device for generating vacuum but is preferably a vacuum chip or a venturi chip that generates vacuum when isolation valve 14 and vacuum proportional valves 16 and/or 18 are open and gas from pressurized gas source 12 is passed through vacuum generator 22. Pressure transducer 24 may be any suitable device for directly or indirectly measuring pressure and vacuum. Fluid level sensor 28 may be any suitable device for measuring the level of a fluid 42 within aspiration chamber 26 but is preferably capable of measuring fluid levels in a continuous manner. Fluid level sensor 28 is most preferably an optical sensor capable of measuring fluid levels in a continuous manner. Pump 30 may be any suitable device for generating vacuum but is preferably a peristaltic pump, a scroll pump, or a vane pump. Microprocessor 38 is capable of implementing feedback control, and preferably PID control. Proportional controller 40 may be any suitable device for proportionally controlling system 10 and/or surgical device 36 but is preferably a foot controller.

System 10 preferably utilizes three distinct methods of controlling aspiration, vacuum control, suction control, and flow control. These methods are more fully described in co-pending U.S. application Ser. No. 11/158,238 filed Jun. 21, 2005 and co-pending U.S. application Ser. No. 11/158,259 filed Jun. 21, 2005, both of which are commonly owned with the subject application and are incorporated herein by reference.

In each of these methods, vacuum may be provided to surgical device 36 and aspiration chamber 26 via fluid lines 50, 56, and 58. Aspiration chamber 26 fills with fluid 42 aspirated by surgical device 36. Fluid 42 includes liquid infusion fluid as well as aspirated ophthalmic tissue. Aspiration chamber 26 is comprised of a storage portion 130 and a sensing portion 132. Storage portion 130 has a larger transverse cross sectional area than that of sensing portion 132. The transverse cross sectional area of storage portion 130 is preferably up to 7.5 times larger than that of sensing portion 132, and is most preferably about 7.5 times larger than that of sensing portion 132. Storage portion 130 and sensing portion 132 are fluidly coupled. The angle between storage portion 130 and sensing portion 132 is most preferably about 90 degrees. As is visible in FIG. 2, aspiration chamber 26 is oriented so that storage portion 130 is toward the top of surgical cassette 100.

As shown in FIGS. 2 and 3, a surgical cassette 100 has a body 102 including aspiration chamber 26. A cover, which is fluidly sealed to the front side of body 102, is not shown for purposes of clarity. A pinch plate, which is fluidly sealed to the rear side of body 102, is not shown for purposes of clarity. A port 108 is fluidly coupled to fluid line 50. An entry 110 fluidly couples sensing portion 132 of aspiration chamber 26 and fluid line 56. As discussed hereinabove, fluid line 56 is fluidly coupled to surgical device 36 via port 34 and fluid line 58. An entry 112 fluidly couples sensing portion 132 of aspiration chamber 26 and fluid line 52. Aspiration chamber 26; ports 32 and 34; fluid lines 52, 54, and 56; port 108; entry 110; and entry 112 are preferably integrally molded into body 102.

During operation, a vacuum is supplied to aspiration chamber 26. Fluid 42 is directed from surgical device 36 to aspiration chamber 26. Aspiration chamber 26 has dual functionalities. One of these functions is to support continuous level sensing from which a measurement of flow rate can be determined. The flow measurement may be obtained as follows:

$$Q = A \times \frac{\Delta L}{\Delta t}$$

where Q is the flow rate, A is the cross sectional area of sensing portion 132, $\Delta L$ is the measured change of fluid level by fluid level sensor 28, and $\Delta t$ is the change in time. It is critical to have an accurate and precise measurement of the level of fluid 42 in aspiration chamber 26. To improve the sensitivity of the flow measurement, the transverse cross sectional area of aspiration chamber 26 perpendicular to fluid level sensor 28 needs to be small. This functionality is accomplished by sensing portion 132 of aspiration chamber 26. Fluid 42 enters sensing portion 132 of aspiration chamber 26 via entry 110. The smaller cross sectional area of sensing portion 132 enables fluid level sensor 28 to accurately and precisely determine the fluid level change within aspiration chamber 26. Another function of aspiration chamber 26 is to hold additional fluid 42 to support a non-interrupted surgical procedure during exchange of a collection bag (not shown) fluidly coupled to collection bag port 32. If, during a surgical procedure, a need exists to store fluid within aspiration chamber 26, as would be the case during a collection bag exchange, the storage portion 130 of aspiration chamber 26 provides a large cross sectional which can provide ample volume for fluid storage.

The present invention is illustrated herein by example, and various modifications may be made by a person of ordinary skill in the art. For example, the present invention may be implemented into an infusion chamber 26 of a surgical cassette having both a storage portion 130 and a sensing portion 132, versus an aspiration chamber 26 as described hereinabove.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A surgical cassette having an aspiration chamber disposed therein, said aspiration chamber comprising:
  a fluid level sensing portion having a first transverse cross sectional area, said sensing portion providing accurate and precise evidence of continuous fluid level changes during use of said cassette; and
  a storage portion fluidly coupled to said sensing portion during application of vacuum to said aspiration chamber and having a second transverse cross sectional area larger than said first transverse cross sectional area, said storage portion providing adequate fluid storage during use of said cassette;
  whereby said sensing portion is disposed proximate a bottom of said aspiration chamber so that a surgical aspiration fluid first enters said sensing portion at a bottom of said aspiration chamber and substantially fills said sensing portion before entering said storage portion, said storage portion being disposed proximate a top of said aspiration chamber;
  whereby said first transverse cross sectional area provides improved measurement sensitivity of both said continuous fluid level changes and a calculated aspiration flow rate of said surgical fluid; and
  whereby said second transverse cross sectional area provides a sufficient amount of said surgical fluid to support a non-interrupted surgical procedure during exchange of a collection bag fluidly coupled to said aspiration chamber.

2. The surgical cassette of claim 1 wherein said second transverse cross sectional area is approximately 7.5 times larger than said first cross sectional area.

3. The surgical cassette of claim 1 wherein the angle between said sensing portion and said storage portion is about 90 degrees.

4. The surgical cassette of claim 1 wherein said aspiration chamber is not vented to atmosphere.

* * * * *